United States Patent [19]

Nishikawa et al.

[11] Patent Number: 4,897,257

[45] Date of Patent: Jan. 30, 1990

[54] METHOD FOR PRODUCING FOAMABLE COMPOSITION

[75] Inventors: Hirokazu Nishikawa, Minamikawachi; Junzou Yamashita, Toyonaka; Hiroshi Kimura, Suita, all of Japan

[73] Assignee: Takeda Chemical Industries, Ltd., Osaka, Japan

[21] Appl. No.: 282,989

[22] Filed: Dec. 2, 1988

Related U.S. Application Data

[63] Continuation of Ser. No. 822,226, Jan. 24, 1986, abandoned.

[30] Foreign Application Priority Data

Feb. 7, 1985 [WO] PCT Int'l Appl. ... PCT/JP85/00050
Nov. 8, 1985 [WO] PCT Int'l Appl. ... PCT/JP85/00625

[51] Int. Cl.$^4$ .......................... A61K 9/46; A61K 9/20; A61K 31/375
[52] U.S. Cl. ........................................ 424/44; 514/474
[58] Field of Search ........................... 424/44; 514/474

[56] References Cited

U.S. PATENT DOCUMENTS

| | | | |
|---|---|---|---|
| 2,071,841 | 2/1937 | Kelling | 99/140 |
| 2,999,293 | 9/1961 | Taff et al. | 424/44 |
| 3,653,914 | 4/1972 | Schmitt | 424/44 |
| 3,773,922 | 11/1973 | Gergely et al. | 424/44 |
| 4,265,847 | 5/1981 | Hunt | 424/44 |
| 4,384,005 | 5/1983 | McSweeney | 426/250 |
| 4,417,993 | 11/1983 | Gergely | 424/44 |
| 4,508,740 | 4/1985 | McSweeney | 426/250 |
| 4,619,829 | 10/1986 | Motschan | 424/602 |
| 4,678,661 | 7/1987 | Gergely et al. | 424/44 |
| 4,687,662 | 8/1987 | Schobel | 424/44 |
| 4,800,086 | 1/1989 | Buehler et al. | 424/497 |
| 4,812,303 | 3/1989 | Ioriu et al. | 424/44 |
| 4,830,862 | 5/1989 | Braun et al. | 426/74 |
| 4,832,956 | 5/1989 | Gergely et al. | 424/466 |

FOREIGN PATENT DOCUMENTS

| | | |
|---|---|---|
| 6144496 | 1/1961 | Belgium . |
| 1363117 | 6/1964 | France . |
| 2044216 | 2/1971 | France . |
| 1328591 | 8/1973 | United Kingdom . |
| 1359614 | 7/1974 | United Kingdom . |

Primary Examiner—Shep K. Rose
Attorney, Agent, or Firm—Wenderoth, Lind & Ponack

[57] ABSTRACT

Rapidly-disintegratable active-component-containing foamable compositions can be obtained by mixing an active component (Component-C) into a solid alkali metal or alkaline earth metal salt of carbonic acid (Component-A) and/or a solid aliphatic carboxylic acid (Component-B), and then mixing component-A and Component-B together after being moisturized separately with approx. 0.5–5% (w/w) water.

10 Claims, No Drawings

METHOD FOR PRODUCING FOAMABLE COMPOSITION

This application is a continuation, of now abandoned application Ser. No. 822,226, filed Jan. 24, 1986.

The present invention relates to foamable compositions with excellent quality in that they disintegrate to foam in a short time.

A wide variety of methods for producing foamable compositions are known, French Pat. No. 69.15360 (Laid Open No. 2,044,216) and U.S. Pat. No. 3,773,922 being especially notable. In these patented methods, foamable components, i.e. a carbonic acid compound and an acid compound, are moisturized with a small amount of water to obtain tablets as final products.

In the said French-patented method, a powdered base component and a powdered acid component are separately moisturized with water, mixed together and dried. The resulting dry mixture, after a medicinal component is added, is tableted into foamable tablets.

This method, however, has some drawbacks, e.g. the moisturized granules are extremely fine. In addition, the powder ratio is too high due to the medicinal component which is added after the moisturization/drying processes. These factors cause various disadvantages such as adhesion and die friction in the tableting process. When the powder ratio is too high (40% or more), tableting is sometimes impossible because powder mixture fluidity is so degraded that the powder mixture does not flow out of the tableting machine hopper.

In the method specified in U.S. Pat. No. 3,773,922, a carbonic acid compound, an acid compound and a medicinal component are mixed, granulated and moisturized, and then the resulting granules after being dried, are tableted to produce foamable tablets.

However, this method, in which water is added in a ratio of 1 wt. % or less to the amount of an alkali bicarbonate, also has some problems. When the total amount of a medicinal component and citric acid added exceeds the amount of the alkali bicarbonate added, the ratio of water added to the whole weight equals that obtained in the said French-patented method (0.5% or less). This means that nothing but extremely fine particles are produced as shown above; adhesion or die friction is caused in the tableting process because the effect of the lubricant is weakened. To obtain granules, water is vaporized in different ratios to the acid-alkali mixture; however, specially-designed equipment is required so this method is not recommended. In addition, moisturization with water vapor requires more time than that by water addition and it is difficult to control the moisture of the granules. As a working example shown in the said U.S. Patent, dry citric anhydride is added after sodium bicarbonate is moisturized. In this case, it is difficult to obtain a uniform mixture; until the citric anhydride is completely moisturized by the moisturized sodium bicarbonate, the acid-alkali reaction does not proceed uniformly because there is an uneven water distribution in the citric anhydride.

The inventors, after studying how to produce a quickly-decomposable, fast-foamable and easily-producible foamable composition, found that a foamable composition satisfying the said requirements can be produced via a process in which an active component is mixed into a carbonic acid compound or an acid compound or to both and then mixed with each other after being separately moisturized with approx. 0.5~5% water. The inventors then completed this invention after further studies.

The present invention is a method for producing an active-component-containing foamable composition, characterized in that an active component (Component-C), and a binder, if necessary, is mixed into a solid alkali metal or alkaline earth metal salt of carbonic acid (Component-A, hereinafter called "alkali component" in some cases) or a solid aliphatic carboxylic acid (Component-B, hereinafter called "acid component" in some cases) or to both, and they are mixed with each other after being separately moisturized with approx. 0.5—5% (w/w) water relative to the mixture.

Alkali metal carbonates, alkali metal bicarbonates, alkaline earth metal carbonates, etc. can be used as the alkali component.

Sodium, potassium, etc. and calcium, magnesium, barium, etc. can be listed as alkali metals and alkaline earth metals, respectively.

As alkali metal carbonates, sodium carbonate, potassium carbonate, etc. can be used, sodium carbonate being especially preferable. As alkali metal bicarbonates, sodium bicarbonate, potassium bicarbonate, etc. can be used, sodium bicarbonate being especially preferable. As alkaline earth metal salts, calcium carbonate, magnesium carbonate, barium carbonate, etc. can be used, calcium carbonate being especially preferable.

A mixture of the said compounds can be used as the alkali component.

The alkali component must be solid, e.g. powdered salts and granulated salts; granulated ones being especially preferable.

As the aliphatic carboxylic acids used in this invention, monobasic, dibasic, tribasic, etc. are listed below.

These aliphatic carboxylic acids are those having 2-10 carbon atoms, preferably 2-6 carbon atoms.

As monobasic aliphatic carboxylic acids, glacial acetic acid, glycolic acid, etc. can be used. As dibasic aliphatic carboxylic acids, tartaric acid, fumaric acid, maleic acid, malonic acid, malic acid, succinic acid, etc. can be used. As tribasic aliphatic carboxylic acids, citric anhydride, citric acid, isocitric acid, etc. can be used.

A mixture of the said compounds can be used as an aliphatic carboxylic acid. Among the aliphatic carboxylic acids shown above, citric anhydride is especially preferable.

As solid aliphatic carboxylic acids, powdered ones, granulated ones, etc. can be used; granulated ones being especially preferable.

The desirable ratio of Component-A to Component-B is approx. 1:1~1:2 (w/w).

As active components, medicines, foods, agricultural chemicals, drugs for animals, etc. can be used.

As medicines, vitamin C (L-ascorbic acid, sodium L-ascorbate, calcium L-ascorbate), para-acetamol (acetaminophen), aspirin (acetylsalicylic acid), their combinations, multi-vitamin compounds [e.g. vitamins A, $B_1$, $B_2$, $B_3$, $B_5$, $B_6$, $B_{12}$, C, D and E, folic acid, and minerals (e.g. iron, calcium, copper, potassium, magnesium, manganese, zinc, and iodine)], etc. can be used.

When a medicine is used as an active component, the desirable ratio to the foamable components (Component-A and Component-B) is approx. 40% or less (by weight).

As foods, powdered liquor, aspartame ($\alpha$-L-aspartyl-L-phenylalanine methyl ester), acesulfam [6-methyl-1,2,3-oxathiazine-4-(3H)-one-2,2-dioxan] or its alkali metal salts (potassium salt, etc.), sweetening agents such as saccharin and sugar, vitamin/mineral mixtures such as sports drinks, teas containing crude-drug extracts, etc. can be used.

When a food is used as an active component, the desirable ratio to the foamable components (Component-A and Component-B) is approx. 60% or less (by weight).

As agricultural chemicals to be added, gibberellic acid, etc. can be used. When an agricultural chemical is added as an active component, the recommended ratio to the foamable components (Component-A and Component-B) is approx. 60% or less (by weight).

As drugs for animals to be added, nitrofurazone, sulfadimethoxine, furazolidone, chlorotetracycline, etc. can be used.

When a drug for animals is added as an active component, the recommended ratio to the foamable components (Component-A and Component-B) is approx. 60% or less (by weight).

Active components to be used in this invention can be powdered or granulated, granulated ones being especially preferable.

As for the addition of an active component, it is recommended that a basic active component is mixed with the alkali component (Component-A). It is recommended that an acid active component is mixed with an aliphatic carboxylic acid (Component-B). A neutral active component can be mixed with Component-A or Component-B or with both.

The compositions obtained in this invention can assume such forms as tablets and granules.

The method for producing the foamable composition is hereinafter described. An active component and a binder, if necessary, are added to the alkali component (Component-A). The resulting mixture is moisturized with approx. 0.5~5% (w/w) water. As binders to be added, polyvinyl pyrrolidone, dextrin, dextrose, lactose, acacia powder, methyl cellulose, hydroxypropyl methyl cellulose, etc. can be used.

A desirable amount of water used for moisturization is approx. 1~3% (w/w), preferably approx. 1~2% (w/w). An organic solvent can be added to the water, if required. As organic solvents, ethanol, acetone, etc. can be used. In such cases, the recommended ratio of water to the organic solvent is approx. 1:1~1:4 (v/v).

Coloring agents, sweetening agents, etc. can be added to the water to make a solution. As coloring agents, riboflavin, synthetic coloring agents such as tartrazine and sunset yellow, etc. can be used. As sweetening agent, saccharin, aspartame, sugar, etc. can be used.

As for moisturization methods, water is sprayed or little by little dropped, with the component mixture being stirred in a stirrer.

An active component, if required, and a binder, if further required, are added to a solid aliphatic carboxylic acid (Component-B), the resulting mixture being moisturized with approx. 0.5~5% (w/w) water.

As binders to be added, those used in the process of moisturizing Component-A can be used as well.

A desirable amount of water used for moisturization is approx. 1~3% (w/w), preferably approx. 1~2% (w/w).

An organic solvent, if required, can be added to the water. As organic solvents, those used in the process of moisturizing Component-A can be used as well. The desirable amount of the organic solvent is equal to that used in the moisturization process.

Component-A and Component-B either or both of which now contain Component-C, after being separately moisturized, are mixed with each other. For example, they are stirred and mixed in a vessel such as a Vertical Granulator (Fuji Industries Co., Ltd., Japan) for approx. 3~5 minutes.

Usually, the resulting granules are immediately subjected to the next process; however, it is preferable that they be sieved so that they can pass through an 8-mesh sieve (JIS) but cannot pass through a 100-mesh sieve (JIS).

The resulting granules are next subjected to the drying process. For example: they are dried in a vacuum oven at approx. 40°~60° C. and approx. 0~5 mmHg, for approx. 8~16 hours; or dried in a forced-convention oven at approx. 40°~60° C. for about 1~3 hours.

When granules for tableting are prepared, a diluted lubricant may be added to foamable granules containing the acid component and the alkali component. The lubricant may be diluted with, for example, the acid component, the alkali component, a perfume or a binder shown below. In this case, the lubricant should be uniformly dispersed. This is because a lubricant, when directly mixed with foamable granules, is liable to become large spherical granules in the presence of static electricity. That is, by preventing the granulation of the lubricant itself in the said procedure, the effect of the lubricant is improved so that the mixture can be easily tableted. In addition, the foamable power of tablets to be produced can be improved by adding an alkali metal carbonate that has been granulated separately.

The dry granules prepared via the said processes are then tableted. To the granules, if desired, coloring agents, perfumes, sweetening agents, seasonings, binders, compression lubricants, etc., can be added prior to the tableting process.

As coloring agents, riboflavin, tartrazine, sunset yellow, etc., can be used. As perfumes, orange oil, lemon oil, orange powder, lemon powder, etc., can be used. As sweetening agents, saccharin, Aspartame, sugar, etc., can be used. As seasonings, sodium glutamate, nucleic acid seasonings, succinic acid, powdered bonito broth, etc., can be used.

When an agricultural chemical is added as an active component, an emulsifier, etc. can be added to make tablets. As emulsifiers, sodium laurylsulfate, polyvinyl pyrrolidone, polyethylene glycol, fatty acid ester of polyhydric alcohol such as Span (sorbitan fatty acid ester, Atlas Powder Co., USA) and Tween (polyoxyethylene sorbitan fatty acid ester, Atlas Powder Co., USA), sugar ester, etc., can be used.

When a drug for animals is added as an active component, an emulsifier, etc. can be added to make tablets. As emulsifiers, sodium laurylsulfate, polyvinyl pyrrolidone, polyethylene glycol, fatty acid ester of polyhydric alcohol such as Span and Tween, sugar ester, etc., can be used.

As binders used in the tableting process, polyvinyl pyrrolidone, dextrin, acacia powder, methyl cellulose, hydroxypropyl methyl cellulose, sugar, etc., can be used.

As compression lubricants used in the tableting process, sodium stearate, sodium benzoate, polyethylene glycol 4000, polyethylene glycol 6000, etc., can be listed.

A conventional method is used in the tableting process.

When a medicine is the active component of the foamable composition, the composition containing an effective dose of the medicine is administered in the following manners:

The composition is put into the mouth, foamed, dissolved or suspended, and then swallowed (oral administration).

The composition is put into water, foamed, and dissolved or suspended; the resulting liquid (solution or suspension) being orally administered.

The composition is put into water, foamed, and dissolved or suspended, the resulting liquid (solution or suspension) being applied to the skin (percutaneous administration).

The composition is put into hot water in a bathtub, foamed, and dissolved or suspended; the medicinal component being percutaneously absorbed.

The composition (tablet) is inserted into the vagina, foamed, and dissolved or suspended; the medicinal component being absorbed there.

As a concrete example: 1~2 foamable tablets containing approx. 500~1,000 mg of ascorbic acid per tablet are put into approx. 60~200 ml water to foam and dissolve, the resulting solution being orally administered.

When a foodstuff is the active component of the foamable composition, a composition which contains an effective amount of the foodstuff is used in the following manners:

The composition is put into the mouth, where it foams and dissolves or suspends, and is then swallowed.

The composition is put into water, foamed, and dissolved or suspended; the resulting liquid (solution or suspension) being swallowed.

The composition is added to or sprinkled over cooking materials during cooking.

The composition (granules) is sprinkled over washed vegetables.

As a concrete example: 1~2 foamable tablets containing approx. 500~1,000 mg/tablet of a tea containing crude-drug extracts are put into approx. 60~100 ml hot water at 40°~80° C., foamed and dissolved, the resulting solution being swallowed.

When an agricultural chemical is the active component of the foamable composition, a composition that contains an effective amount of the agricultural chemical is used in the following manner, for example: the composition is put into water and foamed, the resulting liquid (solution or suspension) being spread over the object, animals or plants to be treated.

When a drug for animals is the active component of the foamable composition, the composition in an amount that contains an effective dose of the drug is administered to the animal in the following manners:

The composition is put into water and foamed, the resulting liquid (solution or suspension) being orally administered to the animal.

The composition is put into water and foamed, the resulting liquid (solution or suspension) being sprayed over the animal.

The composition is put into water in a water tank, foamed, and dissolved or suspended; the animal being made to bathe in the resulting liquid.

When the foamable composition is used in the form of granules, the granules are not only easily strip-wrapped but also unsatisfactory adhesion due to the sticking of fine particles to the wrapping-film connections is never caused. Therefore, the granules can be easily handled. This is because the granules are uniform in size with few fine particles.

In addition, their size is sufficiently large so that they sink and then foam well when put into water.

Because the amount of water required in granulating the composition is so little the granules can be easily dried. Because uniform granules are obtainable by mixing a moisturized acid component and a moisturized alkali component, the uniformization process, which is required prior to the drying process in ordinary granulation processes can be omitted. In addition, the granules, after being dried, can be easily uniformized by sieving because they do not adhere to each other. For these reasons the foamable composition can be easily granulated on an industrial scale.

In conventional methods, an acid component and an alkali component should be separately kneaded, granulated, dried, and uniformized, to produce foamable tablets. In the present method, however, the two components can be mixed with each other prior to the kneading, granulating, drying and uniformization processes, i.e. the number of processes can be reduced.

The granules obtained by the present method contain few fine particles. Therefore, since a smaller amount of a lubricant is required, the granules are favorably tabletable. In addition, adhesion and die friction can be prevented.

The granules obtained by the present method satisfy the requirements of foamable tablets; they are easily decomposed in water and remain settled at the bottom for long periods of time.

In the present method, the hardness of a tablet can be properly changed between approx. 2 kg and 15 kg. The decomposition time, which increases in proportion to the hardness, can be also controlled according to the intended purpose.

In the present method, the foaming state of a tablet can also be controlled: when its hardness is 2~4 kg, the tablet forms a great amount of fine foam which decomposes within a minute; when the hardness is 5 kg or more, the tablet forms a coarser foam and its disintegration time exceeds 1 minute.

When 10 foamable tablets containing vitamin C obtained by the present method are stored with silica gel in a screwcapped bottle at 60° C. for 1 month, no considerable change is caused in their color, taste, foaming state, foaming time and vitamin C content. Therefore, it is thought that vitamin C-containing foamable tablets obtained by the present method can be kept stable at room temperature for at least 2~3 years in the above packing form. Vitamin C is particularly likely to discolor and is sensitive against heat and moisture, but can be kept stable in the said tablet.

The compositions obtainable by the present invention can be effectively used as rapidly-disintegrating/foamable compositions of medicines, foods, agricultural chemicals or drugs for animals.

The present invention is hereinafter more concretely described with examples. The percentages shown are indicated by weight (w/w %) unless specified.

EXAMPLE 1

Foamable tablets with the following composition (Composition-A) were produced.

| Composition-A | | |
|---|---|---|
| C-97[(1)] | 515.5 mg | (500 mg as vitamin C) |

-continued

| Composition-A | | |
|---|---|---|
| Citric anhydride[2] | 300 mg | |
| Sodium bicarbonate[3] | 550 mg | |
| Saccharin sodium | 10 mg | |
| Sodium benzoate | 50 mg | |
| Total | 1,425.5 mg | (per tablet) |

[1]C-97: Granules containing L-ascorbic acid and cornstarch in a ratio of 97% (w/w) to 3% (w/w), produced by the method shown in Example 1, Japanese Pat. Publication No. 403/1983: Also used in the following examples 2~4 and 9~10.
[2]Granulated citric anhydride which could pass through a 40-mesh sieve (JIS) was used, and was also used in the following examples 2~10.
[3]Granulated sodium bicarbonate which could pass through a 40-mesh sieve (JIS) was used, and was also used in the following examples 2~10.

Production Method (1) 5 g of sunset yellow was dissolved in water to make 100 ml of colored water. 1.8 kg of sodium bicarbonate was stirred in a Vertical Granulator at 600 rpm for 5 minutes, and was stirred for 5 more minutes while 18 ml of the said colored water was added little by little. Separately, 2.062 kg of C-97 and 1.2 kg of powdered citric anhydride were stirred in a Vertical Granulator at 600 rpm for 5 minutes, and was stirred for 5 more minutes while 33 ml of the said colored water was added little by little. The two resulting mixtures were mixed together for 3 minutes.

The resulting mixture was dried in a vacuum oven at 40° C./5 mmHg for 16 hours to produce foamable granules.

(2) 1 kg of sodium bicarbonate was stirred in a Vertical Granulator at 600 rpm for 5 minutes, and was stirred for 5 more minutes while 10 ml of the said colored water was added little by little.

The resulting moisturized colored sodium bicarbonate was dried in a vacuum oven at 40° C. and 5 mmHg for 16 hours to produce colored sodium bicarbonate.

(3) 400 g of the colored sodium bicarbonate, 40 g of saccharin sodium powder and 200 g of sodium benzoate, were mixed and sieved 3 times by a 32-mesh sieve (JIS). 586 g of the resulting mixture and 5,000 g of the foamable granules obtained in (1) were stirred and mixed with each other in a Vertical Granulator at 600 rpm for 3 minutes in a room at 50% relative humidity.

(4) A Stokes-B2 (F. J. Stokes Corp., USA) was used as a tableting machine. Dry compressed air (22° C., 10% relative humidity) was blown around the tableting table of the tableting machine to keep the relative humidity near the pounder at 10%. The mixture obtained in (3) was tableted at 14 rpm using a corner-rounded pounder.

The diameter, thickness, weight and hardness of the resulting foamable tablets, and the foaming time, foaming state, pH and taste of them when they are dissolved in 100 ml of water at 24° C. under normal pressure, are shown in the following.

| Diameter (mm) | Thickness (mm) | Weight (g) | Hardness (kg) | Foaming time | Foaming state | pH | Taste |
|---|---|---|---|---|---|---|---|
| 15.10 | 6.01 | 1.457 | 5 | 1'20" | Good | 5.62 | Sweet |

EXAMPLE 2

Foamable tablets with the following composition (Composition-B) were produced.

| Composition-B | | |
|---|---|---|
| C-97 | 515.5 mg | (500 mg as vitamin C) |
| Citric anhydride | 450 mg | |
| Sodium bicarbonate | 525 mg | |
| Saccharin sodium | 7.5 mg | |
| Cidercorton (perfume) | 22.5 mg | |
| Sodium benzoate | 50 mg | |
| Total | 1,570.5 mg | (per tablet) |

Production Method (1) 5 g of sunset yellow was dissolved in water to make 100 ml of colored water. 1.5 kg of sodium bicarbonate was stirred in a Vertical Granulator at 600 rpm for 5 minutes, and was stirred for 5 more minutes while 15 ml of the said colored water was added little by little. Separately, 2.062 kg of C-97 and 1.8 kg of citric anhydride were stirred in a Vertical Granulator at 600 rpm for 5 minutes, and were stirred for 5 more minutes while 38 ml of the said colored water was added little by little. The two resulting mixtures were mixed together and stirred for 3 minutes.

The resulting mixture was dried in a vacuum oven at 40° C./5 mmHg for 16 hours to produce foamable granules.

(2) 1 kg of sodium bicarbonate was stirred in a Vertical Granulator at 600 rpm for 5 minutes, and was stirred for 5 more minutes while 10 ml of the said colored water was added little by little.

The resulting moisturized colored sodium bicarbonate was dried in a vacuum oven at 40° C./5 mmHg for 16 hours to produce colored sodium bicarbonate.

(3) 600 g of the colored sodium bicarbonate, 30 g of saccharin sodium power, 200 g of sodium benzoate powder and 90 g of cidercorton were mixed and sieved 3 times by a 32-mesh sieve (JIS). 920 g of the resulting mixture and 5,000 g of the foamable granules obtained in (1) were stirred and mixed in a Vertical Granulator at 600 rpm for 3 minutes in a room at 50% relative humidity.

(4) A Stokes-B2 was used as a tableting machine. Dry compressed air (22° C., 10% relative humidity) was blown around the tableting table to keep the relative humidity near the pounding bed at 10%.

Using a corner-rounded pounder having a 15 mm diameter, the mixture obtained in (3) was tableted at 14 rpm.

The diameter, thickness, weight and hardness of the foamable tablets obtained, and their foaming time, foaming state, pH and taste when they are dissolved in 100 ml of water at 24° C. under normal pressure, are as follows:

| Diameter (mm) | Thickness (mm) | Weight (g) | Hardness (kg) | Foaming time | Foaming state | pH | Taste |
|---|---|---|---|---|---|---|---|
| 15.15 | 6.11 | 1.60 | 7 | 1'10" | Good | 4.77 | Slightly sour |

EXAMPLE 3

Foamable tablets with the following composition (Composition-C) were produced.

| Composition-C | | |
|---|---|---|
| C-97 | 515.5 mg | (500 mg as vitamin C) |
| Citric anhydride | 450 mg | |
| Sodium bicarbonate | 500 mg | |
| Saccharin sodium | 5 mg | |
| Cidercorton (perfume) | 22.5 mg | |
| Sodium benzoate | 50 mg | |
| Total | 1,543 mg | (per tablet) |

Production method (1) 5 g of sunset yellow was dissolved in water to make 100 ml of colored water.

1.8 kg of sodium bicarbonate was stirred in a Vertical Granulator at 600 rpm for 5 minutes, and was stirred for 5 more minutes while 18 ml of the said colored water was added little by little.

Separately, 2.062 kg of C-97 and 1.8 kg of powdered citric anhydride were stirred in a Vertical Granulator at 600 rpm for 5 minutes, and were stirred for 5 more minutes while 32 ml of the said colored water was added little by little. The two resulting mixtures were mixed together and stirred for 3 minutes.

The resulting mixture was dried in a vacuum oven at 40° C./5 mmHg for 16 hours to produce foamable granules.

(2) 1 kg of sodium bicarbonate was stirred in a Vertical Granulator at 600 rpm for 5 minutes, and was stirred for 5 more minutes while 10 ml of the said colored water was added little by little.

The resulting moisturized colored sodium bicarbonate was dried in a vacuum oven at 40° C./5 mmHg for 16 hours to obtain colored sodium bicarbonate.

(3) 200 g of the colored sodium bicarbonate obtained in (2), 20 g of powdered saccharin sodium, 200 g of powdered sodium benzoate and 90 g of powdered cidercorton, were mixed together and sieved 3 times by a 32-mesh sieve (JIS). 451 g of the resulting mixture and 5,000 g of the foamable granules obtained in (1) were mixed together and stirred in a Vertical Granulator at 600 rpm for 3 minutes in a room at 50% relative humidity.

(4) A Stokes-B2 was used as a tableting machine. Dry compressed air (22° C., relative humidity: 10%) was blown around the tableting table of the machine to keep the relative humidity near the pounder bed at 10%. The mixture obtained in (3) was tableted at a rate of 14 rpm, using a round-cornered pounder having a 15 mm diameter.

The diameter, thickness, weight and hardness of the foamable tablets obtained, and their foaming time, foaming state, pH and taste when they are dissolved in 100 ml of water at 24° C. under normal pressure, are as follows:

| Diameter (mm) | Thickness (mm) | Weight (g) | Hardness (kg) | Foaming time | Foaming state | pH | Taste |
|---|---|---|---|---|---|---|---|
| 15.12 | 6.12 | 1.569 | 7 | 1'25" | Good | 4.66 | Sour |

EXAMPLE 4

Foamable tablets having the following composition (Composition-D) were produced.

| Composition-D | | |
|---|---|---|
| C-97 | 247 mg | (240 mg as vitamin C) |
| Finely-powdered aspirin | 400 mg | |
| Citric anhydride | 1,200 mg | |
| Sodium bicarbonate | 1,800 mg | |
| Polyethylene glycol 6000 | 20 mg | |
| Saccharin sodium | 10 mg | |
| Sodium benzoate | 100 mg | |
| Total | 3,777 mg | (per tablet) |

Production Method (1) 1.8 kg of sodium bicarbonate was stirred in a Vertical Granulator at 600 rpm for 5 minutes, and was stirred for 5 more minutes while 20 ml of water was added little by little.

(2) Separately from (1), 247 g of C-97, 400 g of finely-powdered aspirin, 1,200 g of citric anhydride and 20 g of polyethylene glycol powder were stirred in a Vertical Granulator at 600 rpm for 5 minutes, and were stirred for 5 more minutes while 20 ml of water was added little by little. The resulting mixture was mixed with the moisturized sodium bicarbonate obtained in (1), and stirred for 3 minutes.

(3) The resulting mixture was dried in a vacuum oven at 40° C./5 mmHg for 16 hours.

(4) 3.5 kg of the mixture sieved by a 32-mesh sieve after being dried, 9.3 g of powdered saccharin sodium and 93 g of powdered sodium benzoate were stirred in a Vertical Granulator at 600 rpm for 3 minutes. The resulting mixture was tableted using a flat pounder having a 25 mm diameter to produce foamable tablets (diameter: approx. 25 mm; thickness: approx. 6 mm; weight: 3,800 mg per tablet). Their foaming time when they were dissolved in 100 ml of water at 16° C. under normal pressure was 1 minute 15 seconds.

EXAMPLE 5

Foamable tablets with the following composition (Composition-E) were produced.

| Composition-E | | |
|---|---|---|
| Alcock[1] (powdered liquor) | 1,000 mg | |
| Citric anhydride | 1,000 mg | |
| Sodium bicarbonate | 1,000 mg | |
| Sodium benzoate | 100 mg | |
| Total | 3,100 mg | (per tablet) |

[1]Vodka type, Alcohol content: 30.5 w/w % Refer to Japanese Patent Publication No. 39355/1972.

Production Method (1) 100 g of citric acid and 100 g of Alcock were mixed together, and 3 ml of water was sprayed over the mixture.

(2) Separately from (1), 1 ml of water was sprayed over 100 g of sodium bicarbonate.

(3) The materials obtained in (1) and (2), after being mixed together, were dried in a forced-convection oven at 50° C. for 2 hours.

(4) 250 g of the dried mixture and 8.1 g of powdered sodium benzoate were mixed together, the resulting mixture being tableted using a flat pounder having a 20 mm diameter to produce tablets (diameter: approx. 20 mm; thickness: approx. 7 mm; weight: 3.1 g per tablet; hardness: 5 kg). Their foaming time when they were dissolved in 100 ml of water at 20° C. under normal pressure was 37 seconds.

EXAMPLE 6

Foamable tablets with the following composition (Composition-F) were produced.

| Composition-F | | |
|---|---|---|
| Aspartame (sweetening) | 100 mg | |
| β-lactose | 600 mg | |
| Citric anhydride | 1,200 mg | |
| Sodium bicarbonate | 1,000 mg | |
| Sodium benzoate | 45 mg | |
| Total | 2,945 mg | (per tablet) |

Production Method (1) 10 g of powdered aspartame, 60 g of powdered β-lactose and 120 g citric anhydride were mixed together, and 2 ml of water sprayed over the mixture.

(2) Separately from (1), 1 ml of water was sprayed over 100 g of sodium bicarbonate.

(3) The materials obtained in (1) and (2), after being mixed, were dried in a forced-convection oven at 50° C. for 2 hours.

(4) 250 g of the dried mixture and 3.9 g of powdered sodium benzoate were mixed together. The resulting mixture was tableted using a flat pounder having a 20 mm diameter (diameter: 20.15 mm; thickness: 7.11 mm; weight: 3.0 g; hardness: 4.7 kg). Their foaming time when dissolved in 100 ml water at 25° C. under normal pressure was 2 minutes and 15 seconds.

EXAMPLE 7

Foamable tablets with the following composition (Composition-G) were produced.

| Composition-G | | |
|---|---|---|
| Sports Drink Takeda[1] | 1,300 mg | |
| Citric anhydride | 1,300 mg | |
| Sodium bicarbonate | 500 mg | |
| Sodium benzoate | 45 mg | |
| Total | 3,145 mg | (per tablet) |

| (1): Vitamins/mineral soft drink Containing the following amounts of vitamins and minerals per 13 g: | | | |
|---|---|---|---|
| Vitamin C | 500 mg | Niacin | 13 mg |
| Phosphoric acid | 49 mg | Vitamin B$_1$ | 0.8 mg |
| Sodium | 80 mg | Magnesium | 4 mg |
| Vitamin B$_2$ | 1.1 mg | Potassium | 78 mg |
| Chloride | 106 mg | | |

Production Method (1) 130 g of powdered Sports Drink Takeda and 130 g of citric anhydride were mixed together, and 3 ml of water was sprayed over the mixture.

(2) Separately from (1), 1 ml of water was sprayed over 50 g of sodium bicarbonate.

(3) The materials obtained in (1) and (2), after being mixed together, were dried in a forced-convection oven at 50° C. for 2 hours.

(4) 300 g of the dried mixture and 4.3 g of powdered sodium benzoate were mixed together. Using a flat pounder 20 mm in diameter, the resulting mixture was tableted (diameter: 20.12 mm; thickness: 7.41 mm; weight: 3.15 g; hardness: 6.5 kg). Their foaming time when they were dissolved in 100 ml of water at 25° C. under normal pressure was 1 minute and 10 seconds.

EXAMPLE 8

Foamable tablets with the following composition (Composition-H) were produced.

| Composition-H | | |
|---|---|---|
| Alete Kindertee[1] | 1,400 mg | |
| Citric anhydride | 700 mg | |
| Sodium bicarbonate | 700 mg | |
| Sodium benzoate | 45 mg | |
| Total | 2,845 mg | (per tablet) |

[1]Granulated tea containing extracts from fennel, jasmine, licorice, camomile, anise, thyme, carissa, mint and peppermint; Nestle Alete GmbH, Switzerland.

Production Method (1) 140 g of Alete Kindertee (granules) and 70 g of citric anhydride were mixed together, and 2 ml of water was sprayed over the mixture.

(2) Separately from (1), 1 ml of water was sprayed over 70 g of sodium bicarbonate.

(3) The materials obtained in (1) and (2), after being mixed together, were dried in a forced-convection oven at 50° C. for 2 hours.

(4) 250 g of the dried mixture and 4.0 g of powdered sodium benzoate were mixed together, the resulting mixture being tableted (diameter: 20.19 mm; thickness: 6.53 mm; weight: 2.85 g; hardness: 11 kg) using a flat pounder of 20 mm in diameter. Their foaming time when they were dissolved in 60 ml of water at 50° C. under normal pressure was 50 seconds.

EXAMPLE 9

Foamable tablets with the following composition (Composition-I) were produced as follows.

| Composition-I | | |
|---|---|---|
| L-ascorbic acid | 300 mg | |
| SA-99 (Note) | 795.4 mg | (700 mg as vitamin C) |
| Citric anhydride | 950 mg | |
| Sodium bicarbonate | 950 mg | |
| β-lactose | 574.6 mg | |
| Fumaric acid | 250 mg | |
| Saccharin sodium | 20 mg | |
| Aspartame | 10 mg | |
| Cidercorton (perfume) | 100 mg | |
| Total | 3,950 mg | (per tablet) |

(Note) SA-99: Granules containing sodium L-ascorbate and corn-starch in a ratio of 1% (w/w), produced according to "the method for producing granules by circulating granulation" shown in Japanese Unexamined Patent Laid Open No. 57-59803.

Production method (1) 5 g of sunset yellow was dissolved in water to make 100 ml of colored water. 950 g of sodium bicarbonate was stirred in a Vertical Granulator at 600 rpm for 5 minutes and was stirred for 5 more minutes while 30 ml of the said colored water was added little by little. To the resulting mixture was added 795.4 g of SA-99 and was stirred for 10 minutes, then 374.6 g of β-lactose was added, stirred for 5 minutes and mixed.

Separately, 300 g of C-97 and 950 g of citric anhydride were stirred in a Vertical Granulator at 600 rpm for 5 minutes and was stirred for 5 more minutes while 15 ml of the said colored water was added little by little. To the resulting mixture was added the colored and moistured mixture of sodium bicarbonate, SA-99 and β-lactose and was stirred for 3 minutes.

The resulting mixture was dried in a vacuum oven at 40° C./5 mmHg for 16 hours to produce foamable granules.

(2) 200 g of β-lactose, 250 g of fumaric acid, 20 g of powdered saccharin sodium, 10 g of aspartame and 100 g of cidercorton (perfume) were mixed together and sieved by a 60-mesh sieve (JIS).

516 g of the resulting mixture and 3000 g of the foamable granules obtained in (1) were mixed together and stirred in a Vertical Granulator at 600 rpm for 3 minutes in a room at 50% relative humidity.

(3) A Kikusui No. 8 F-3 (Kikusui factory, Japan) was used as a tableting machine. The mixture obtained in (2) was tableted at a rate of 14 rpm, using a normal pounder having a 23 mm diameter.

The diameter, thickness, weight and hardness of the formable tablets obtained in (2), and their foaming time, foaming state, pH and taste when they are dissolved in 100 ml of water at 24° C. under normal pressure, are as follows:

| Diameter (mm) | Thickness (mm) | Weight (g) | Hardness (kg) | Foaming time | Foaming state | pH | Taste |
| --- | --- | --- | --- | --- | --- | --- | --- |
| 23.15 | 8.24 | 4.066 | 17.48 | 1'38" | Good | 4.52 | Sweet |

EXAMPLE 10

Foamable tablets with the following composition (Composition-J) were produced as follows.

| Composition-J | |
| --- | --- |
| C-97 | 309.3 mg |
| SA-99 | 795.4 mg |
| Citric anhydride | 950 mg |
| Sodium bicarbonate | 950 mg |
| β-lactose | 525.3 mg |
| Fumaric acid | 250 mg |
| Saccharin sodium | 20 mg |
| Cidercorton (perfume) | 100 mg |
| Total | 3,900 mg (per tablet) |

Production Method (1) 5 g of sunset yellow was dissolved in water to make 100 ml of colored water. 950 g of sodium bicarbonate was stirred in a Vertical Granulator at 600 rpm for 5 minutes and was stirred for 5 more minutes while 25 ml of the said colored water was added little by little. To the resulting mixture was added 795.4 g of SA-99 and was stirred for 10 minutes, then 325.3 g of β-lactose was added. Separately, 309.3 g of C-97 and 950 g of citric anhydride were stirred in a Vertical Granulator at 600 rpm for 5 minutes, and was stirred for 5 more minutes while 20 ml of the said colored water was added little by little. To the resulting mixture were added the colored and moistured mixture of sodium bicarbonate, SA-99 and β-lactose and was stirred for 3 minutes.

The resulting mixture was dried in a vacuum oven at 40° C./5 mmHg for 16 hours to produce foamable granules.

(2) 200 g of β-lactose, 250 g of fumaric acid, 20 g of powdered saccharin sodium and 100 g of cidercorton (perfume) were mixed together and sieved by a 60-mesh sieve (JIS) three times.

514 g of the resulting mixture and 3000 g of the foamable granules obtained in (1) were mixed together and stirred in a Vertical Granulator at 600 rpm for 3 minutes in a room at 50% relative humidity.

(3) A Kikusui No. 8 F-3 (Kikusui factory, Japan) was used as a tableting machine. The mixture obtained in (2) was tableted at a rate of 14 rpm, using a normal pounder having a 23 mm diameter.

The diameter, thickness, weight and hardness of the foamable tablets obtained, and their foaming time, foaming state, pH and taste when they are dissolved in 100 ml of water at 27° C. water under normal pressure, are as follows:

| Diameter (mm) | Thickness (mm) | Weight (g) | Hardness (Kg) | Foaming time | Foaming state | pH | Taste |
| --- | --- | --- | --- | --- | --- | --- | --- |
| 23.15 | 8.42 | 3.898 | 10.9 | 1'20" | Good | 4.45 | Sweet |

What we claim is:

1. In a method for producing a foamable composition which comprises mixing Component-A which is a solid alkali or alkaline earth metal salt of carbonic acid, Component-B which is a solid aliphatic carboxylic acid, and Component-C which is vitamin C, the improvement which comprises mixing Component-C into Component-B, and mixing Component-A and the resultant Component-B together after separately moisturizing the Component-A and the resultant Component-B with approximately 0.5-5% (w/w) water, the ratio of Component-A to Component-B being approximately 1:1-1:2 and the ratio of Component-C to the total of Component-A and Component-B being approximately 60% or less by weight.

2. A method as claimed in claim 1, wherein the Component-A is sodium carbonate.

3. A method as claimed in claim 1, wherein the Component-A is sodium bicarbonate.

4. A method as claimed in claim 1, wherein the Component-A is calcium carbonate.

5. A method as claimed in claim 2, wherein the Component-B is citric anhydride.

6. A method as claimed in claim 1, wherein the amount of water used for moisturization is approximately 1-3% (w/w).

7. A method as claimed in claim 1, wherein the Component-A is at least one of sodium carbonate and potassium carbonate.

8. A method as claimed in claim 1, wherein the Component-A is at least one of sodium bicarbonate and potassium bicarbonate.

9. A method as claimed in claim 1, wherein the Component-A is at least one of calcium carbonate, magnesium carbonate and barium carbonate.

10. A method as claimed in claim 1, wherein the Component-B is at least one of glacial acetic acid, glycolic acid, tartaric acid, fumaric acid, maleic acid, malonic acid, malic acid, succinic acid, citric anhydride, citric acid and isocitric acid.

* * * * *